US00PP33338P2

(12) United States Plant Patent
Van Dijk

(10) Patent No.: US PP33,338 P2
(45) Date of Patent: Aug. 10, 2021

(54) ANTHURIUM PLANT NAMED 'ANTHUQCLO'

(50) Latin Name: ***Anthurium andraeanum* L.**
Varietal Denomination: ANTHUQCLO

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,384

(22) Filed: Jan. 6, 2021

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./369, 365
CPC ... A01H 5/02; A01H 5/12; A01H 5/00; A01H 6/10; A01H 6/00
See application file for complete search history.

(56) References Cited

PUBLICATIONS

Upov Pluto Plant Variety Database 20210511, retrieved on May 11, 2021, retrieved from the Internet at https://www3.wipo.int/pluto/user/en/index.jsp, one page. (Year: 2021).*

* cited by examiner

*Primary Examiner* — June Hwu
(74) *Attorney, Agent, or Firm* — Jondle & Associates, P.C.

(57) ABSTRACT

A new *Anthurium* plant named 'ANTHUQCLO' particularly distinguished by having very shiny and medium blistered, strongly concave, dark reddish-brown, cordate, and durable spathes that retain the original color for a very long period of time, shiny, green, and narrowly cordate, durable leaves, red spadices with reddish-brown tips, early and rich flowering continuously throughout the year, and a plant height of 30.0 cm to 35.0 cm is disclosed.

3 Drawing Sheets

Genus and species: *Anthurium andraeanum* L.
Variety denomination: 'ANTHUQCLO'.

BACKGROUND OF THE NEW PLANT

The present invention comprises a new and distinct variety of *Anthurium*, botanically known as *Anthurium andraeanum* L., and hereinafter referred to by the variety name 'ANTHUQCLO'. The new *Anthurium* plant is a product of a planned breeding program conducted by the inventor in Bleiswijk, the Netherlands. The objective of this breeding program was to create a new plant with a height of 30.0 cm to 35.0 cm having very shiny, medium blistered, dark reddish-brown, strongly concave, cordate, and durable spathes.

The new variety originated from a cross-pollination made in December 2009 in Bleiswijk, the Netherlands. The female parent was a dark red *Anthurium* pot plant designated '15776-01' (unpatented), and the male parent was a dark red *Anthurium* pot plant designated '18377-02' (unpatented).

A single plant was selected from the progeny of the stated cross in January 2012. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 1, 2018 (Application no. 2018/2883), by Applicant who obtained the subject matter disclosed directly from the inventor. 'ANTHUQCLO' has not been made publicly available or sold anywhere in the world prior to the effective filing date of this application with the exception of sales or disclosures made one year or less before the effective filing date of this claimed invention by Applicant who obtained 'ANTHUQCLO' directly from the inventor.

SUMMARY OF THE INVENTION

The following are the most outstanding and distinguishing characteristics of this new variety when grown under normal horticultural practices in Bleiswijk, the Netherlands:

1) Very shiny, medium blistered, dark reddish-brown, and cordate spathes;
2) Red spadices with reddish-brown tips;
3) Shiny, green, narrowly cordate leaves;
4) Strongly concave spathe shape in cross section of middle zone; and
5) Spathes positioned slightly above leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 34-week-old plant grown in a greenhouse in Bleiswijk, the Netherlands, in November 2020. Colors in the photographs may differ from the color values cited in the detailed botanical description, which accurately describe the actual colors of the new variety.

DESCRIPTION OF THE NEW VARIETY

Figure 1:
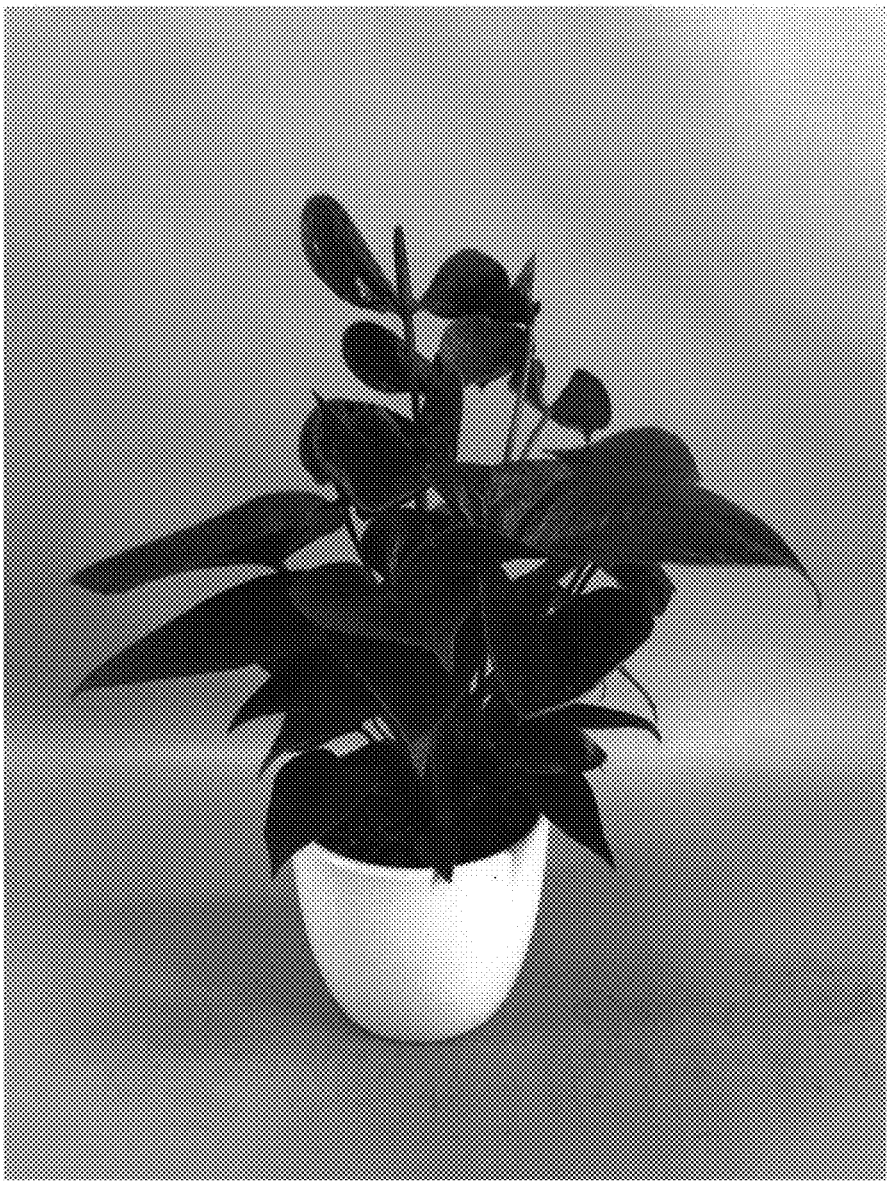
FIG. 1 shows the overall plant habit, including blooms and foliage.
Figure 2:
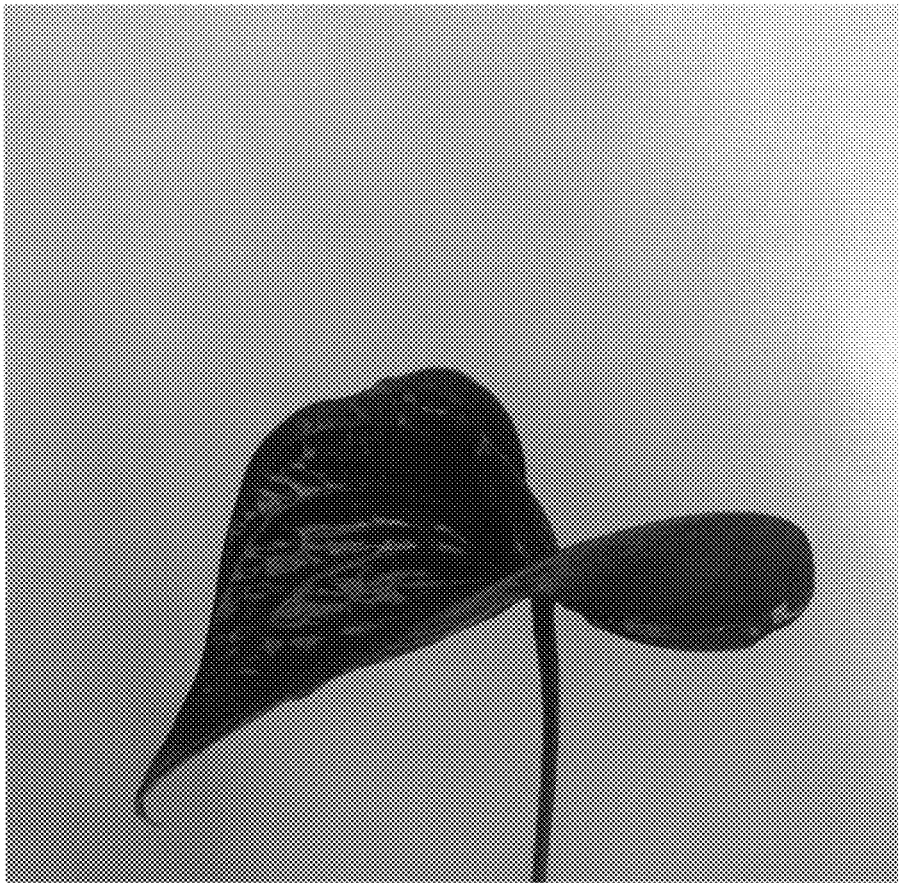
FIG. 2 shows a close-up of the mature spathe.
Figure 3:
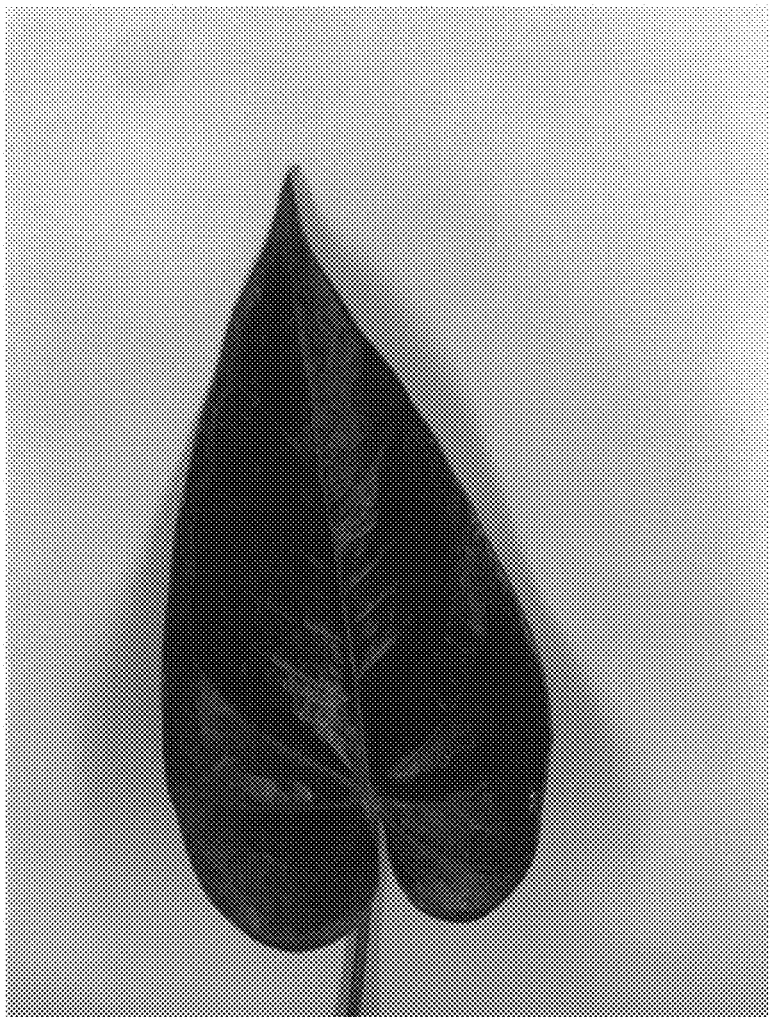
FIG. 3 shows a close-up of the upper leaf blade surface.

The following detailed description sets forth the distinctive characteristics of 'ANTHUQCLO'. The data which define these characteristics were collected from asexual reproductions carried out in Bleiswijk, the Netherlands. The plant history was taken on 34-week-old plants which were planted from tissue culture in 12-centimeter (diameter) pots and grown in a glass greenhouse between 19° C. and 24° C. Observations were made in November 2020. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHUQCLO'.

Parentage:

*Female parent*.—*Anthurium* plant '15776-01' (unpatented).

*Male parent*.—*Anthurium* plant '18377-02' (unpatented).

Plant:

*Propagation*.—Tissue culture.

*Root description*.—Fleshy-creamy (RHS 158C) with a touch of yellowish-pink (RHS 38B) colored roots with small hairy lateral roots having yellow (RHS 12A) colored root tips.

*Time to produce a finished flowering plant*.—32 to 36 weeks after planting in a 12-cm (diameter) pot.

*Growth habit*.—Upright.

*Height* (*measured from soil, including inflorescence*).—30.0 cm to 35.0 cm.

*Width* (*measured from leaf tips*).—33.0 cm to 38.0 cm.

Leaves:

*Immature leaves*.—Length: 12.0 cm to 15.0 cm. Width: 6.0 cm to 8.0 cm. Color: Upper surface: RHS 146A with a touch of RHS N199B. Lower surface: RHS 146B with a touch of RHS N199A. Texture (both upper and lower surfaces): Glossy, leathery, and thin.

*Mature leaves*.—Length (fully expanded): 17.0 cm to 20.0 cm. Width: 9.0 cm to 10.0 cm. Shape: Narrowly cordate. Apex: Acuminate. Base: Cordate. Leaf blade angle with the petiole: Between 115 degrees and 135 degrees. Leaf margin: Entire. Color: Upper surface: RHS 147A. Lower surface: RHS 146A. Texture (both upper and lower surfaces): Glossy, leathery, and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C with a touch of reddish-brown (RHS 175A).

*Lobes*.—Present. Arrangement: Leaf blade has two lobes extending past the petiole. The lobes are non-touching. Length of lobes of mature leaf blades: 2.5 cm to 3.0 cm. Width of lobes of mature leaf blades: 3.5 cm to 4.5 cm. Distance from petiole/leaf junction to highest point on lobes of mature leaf blades: 2.0 cm to 3.0 cm.

*Petiole*.—Cross-section: Round. Diameter: 0.3 cm to 0.4 cm. Length: 15.0 cm to 18.0 cm for a mature leaf size. Color: Mature leaf: RHS 146A. Immature leaf: RHS 146B with a touch of reddish-brown (RHS 175A). Cataphyll color surrounding the petiole: Outside: RHS 144B. Inside: RHS 145B.

*Geniculum*.—Length: 1.5 cm to 2.5 cm. Width: 0.3 cm to 0.5 cm. Color: RHS 146A with a red region (RHS 178A).

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 85 degrees and 95 degrees; the spathe stands on a wiry peduncle about 3.0 cm to 6.0 cm above the foliage.

*Shape*.—Cordate.

*Apex*.—Broad acuminate.

*Base*.—Cordate.

*Texture*.—Medium blistered.

*Margin*.—Undulated.

*Size*.—Length: 9.5 cm to 10.5 cm. Width: 10.5 cm to 11.5 cm.

*Lobes*.—Present. Arrangement: The spathe has two lobes extending past the peduncle. The lobes are non-touching. Length: 1.5 cm to 2.0 cm Width: 4.5 cm to 5.5 cm

*Color*.—Just fully open: Upper surface: Something in between RHS 200A and 187A with a touch of green (RHS 146A) at the margin of lobes. Lower surface: RHS 175A with a hint of RHS 146C toward margin of lobes. This dark red-brown color remains for a very long period, at least more than 30 weeks after opening. The spathe turns green after some weeks.

Peduncle:

*Shape*.—Erect.

*Cross-section*.—Round.

*Length*.—22.0 cm to 25.0 cm.

*Diameter*.—0.3 cm to 0.4 cm.

*Color*.—RHS 144B with a touch of brown (RHS 175A) toward spathe.

Flowering time:

*General*.—One small, rooted, untreated tissue culture plant of 8.0 cm tall will flower, depending on the season, after 32 to 36 weeks and 6 to 7 blossoms appear. More blossoms appear after some additional weeks so that a full flowering and commercial plant will have 7 to 8 dark red-brown spathes. Smaller blossoms may occur on immature plants.

Spadix:

*Size*.—Length: 3.5 cm to 4.5 cm (depending on flower size). Width (at apex): 0.4 cm to 0.5 cm. Width (at base): 0.6 cm to 0.7 cm.

*Shape*.—Columnar.

*Angle of spadix tip with peduncle*.—150 degrees to 160 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 200B. Mature: RHS 183D. Ages to: RHS 184A.

Flowers:

*Quantity per spadix*.—80 to 120.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 183D.

Reproductive organs:

*Stamens*.—Not visible.

*Pollen amount*.—Absent.

*Pistil*.—Quantity: Many. Length: Less than 0.01 cm. Color: RHS 183D.

*Style*.—Not observed to date.

*Stigma*.—Shape: Ovoid. Diameter: Less than 0.01 cm. Color: RHS 183D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHUQCLO' differs from the female parent plant '15776-01' (unpatented) in that 'ANTHUQCLO' has dark reddish-brown spathes that are strongly concave in cross section of the middle zone and short spadices, whereas '15776-01' has dark red spathes that are concave to straight in cross section of the middle zone and very long spadices.

'ANTHUQCLO' differs from the male parent plant '18377-02' (unpatented) in that 'ANTHUQCLO' has dark reddish-brown spathes and short spadices that are red at the base with reddish-brown tips, whereas '18377-02' has dark red spathes and medium long spadices that are white at the base with yellowish-green tips.

'ANTHUQCLO' differs from similar commercial variety 'ANTHCUFPA' (U.S. Plant Pat. No. 28,032) in that 'ANTHUQCLO' has broad acuminate spathe apexes and spadices that are red at the base with reddish-brown tips, whereas 'ANTHCUFPA' has mucronate spathe apexes and spadices that are white at the base with green tips. Additionally, 'ANTHUQCLO' has fewer flowers per spadix than 'ANTHCUFPA'.

'ANTHUQCLO' differs from similar variety 'ANTHFUBE' (U.S. Plant Pat. No. 30,966) in that 'ANTHUQCLO' has broad acuminate spathe apexes and spadices that are red at the base with reddish-brown tips, whereas 'ANTHFUBE' has mucronate spathe apexes and spadices that are yellowish-white at the base with green tips. Additionally, 'ANTHUQCLO' has shorter spadices and fewer flowers per spadix than 'ANTHFUBE'.

I claim:

1. A new and distinct variety of *Anthurium* plant named 'ANTHUQCLO', substantially as illustrated and described herein.

* * * * *